United States Patent
Totoki

(10) Patent No.: US 6,904,787 B2
(45) Date of Patent: Jun. 14, 2005

(54) METHOD FOR MEASURING SUSPENDED PARTICULATE MATTER IN ATMOSPHERIC AIR

(75) Inventor: Shinichiro Totoki, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 10/409,506

(22) Filed: Apr. 8, 2003

(65) Prior Publication Data

US 2003/0200787 A1 Oct. 30, 2003

(30) Foreign Application Priority Data

Apr. 24, 2002 (JP) ........................................ 2002-122557

(51) Int. Cl.$^7$ ................................................. G01N 1/00
(52) U.S. Cl. .................... 73/28.04; 73/28.04; 73/28.01; 73/28.02; 244/1 R
(58) Field of Search ............................. 73/28.04, 28.01, 73/28.02; 244/1 R

(56) References Cited

U.S. PATENT DOCUMENTS 3,828,526 A * 8/1974 King ............................. 96/49
5,344,724 A * 9/1994 Ozaki et al. .................. 429/94
5,678,783 A * 10/1997 Wong .......................... 244/1 R
6,221,136 B1 * 4/2001 Liu et al. ....................... 96/66
6,639,971 B2 * 10/2003 Kwak et al. .................. 379/44

* cited by examiner

*Primary Examiner*—Hezron Williams
*Assistant Examiner*—André K. Jackson
(74) *Attorney, Agent, or Firm*—Rankin, Hill, Porter & Clark LLP

(57) ABSTRACT

Particulate collector is carried onto airplane and collects suspended particulate matter in the atmospheric air in such a manner that suspended particulate matter is electrically charged by single-pole ions generated by a discharge electrode and the thus electrically charged particulates are attracted to a collecting electrode having an electric potential difference with respect to the discharge electrode so that the particulates are collected by the collecting electrode. The particulate collector is conveyed to an arbitrary altitude and driven so as to collect suspended particulate matter contained in the atmospheric air at the arbitrary altitude. Particulate collector is recovered onto the ground so as to make various measurements or the thus collected particulate collector is subjected to various measurements on airplane.

10 Claims, 2 Drawing Sheets

METHOD FOR MEASURING SUSPENDED PARTICULATE MATTER IN ATMOSPHERIC AIR

BACKGROUND OF THE INVENTION

1. Field of the Invention

The present invention relates to a method for measuring suspended particulate matter existing in the atmospheric air.

2. Description of the Related Art

Suspended particulates in the atmospheric air, the diameter of which is not more than 10 μm, are referred to as suspended particulate matter (SPM). Although this suspended particulate matter contains mud which has been rolled up, it primarily contains black smoke, unburned fuel and sulphur compound. In the Kanto District, 35% of them has been exhausted from Diesel engine cars. It is said that those black smoke, unburned fuel and sulphur compound are seriously injurious to human's health. Especially, particulate matter contained in exhaust gas discharged from Diesel engine cars is referred to as DEP. Particulate matter, the particulate diameter of which is small, that is, the particulate diameter of which is not more than 2.5 μm, is referred to as fine particulate matter (PM 2.5), into which investigations have been energetically made in Europe and America. In the case of this PM 2.5, suspended particulate matter is mainly composed of gas exhausted from Diesel engine cars.

Concerning the method for measuring the suspended particulate matter, the following methods are known. When the atmospheric air is sucked on the ground and made to pass through a filter, suspended particulate matter is collected by the filter and observed through a microscope so as to check the profiles and the number of particulates. Alternatively, suspended particulate matter contained in the atmospheric air of a constant volume is collected by a filter by the same method as described above, and the weight of the filter before collecting the suspended particulate matter and the weight after collecting the suspended particulate matter are measured so as to find a quantity of particulates. Alternatively, suspended particulate matter collected by a filter in the same manner is subjected to an appropriate pretreatment, and chemical substance contained in the suspended particulate matter is identified with a gas chromatograph mass spectrometer, a liquid chromatograph mass spectrometer or a spectral analyzer.

In this connection, when the related-art measuring method is adopted in which suspended particulate matter is collected by a filter so as to conduct various measurements on the suspended particulate matter, the following problems may be encountered. For example, in the case of observing particulates through a microscope, images of the particulates become unclear being affected by the filter image in the background. Therefore, it is difficult to observe the image of the particulates.

Further, in the case of measuring a quantity of particulates by measuring the weight of a filter before collecting suspended particulate matter and also by measuring the weight of a filter after collecting suspended particulate matter, since the filter usually tends to absorb water, errors tend to be made by a difference between a quantity of water absorbed before collecting suspended particulate matter and a quantity of water absorbed after collecting suspended particulate matter.

Furthermore, it is difficult for suspended particulate matter, which has been collected by a filter, to exist alone. Accordingly, it is difficult for a single particulate to be irradiated with electromagnetic waves. Therefore, it is difficult for the suspended particulate matter to be subjected to spectral analysis. Further, it is difficult to extract the suspended particulate matter from the filter. Accordingly, it is difficult for suspended particulate matter to be subjected to gas chromatograph mass spectrometer.

Furthermore, according to the related-art method for measuring suspended particulate matter, the suspended particulate matter is collected on the ground. Therefore, only the suspended particulate matter existing close to the ground can be measured.

SUMMARY OF THE INVENTION

The present invention has been accomplished to solve the above related-art problems all at once. It is an object of the present invention to provide a method of capable of accurately measuring and analyzing suspended particulate matter with various measuring apparatus and also capable of measuring suspended particulate matter at an arbitrary altitude.

In order to accomplish the above object, the present invention provides a method for measuring suspended particulate matter in the atmospheric air, the method comprising:

carrying a particulate collector onto an airplane, the particulate collector comprising a discharge electrode and a collecting electrode having an electric potential with respect to the discharge electrode;

conveying the particulate collector to an arbitrary altitude;

driving the particulate collector so as to collect the suspended particulate matter contained in the atmospheric air at the arbitrary altitude in such a manner that the suspended particulate matter is electrically charged by single-pole ions generated by the discharge electrode and the thus electrically charged particulates are attracted to the collecting electrode; and conducting a predetermined measurement on the collected particulate matter with a measuring apparatus according to an object.

In the above-mentioned method for measuring suspended particulate matter in the atmospheric air, it is preferable that the particulate collector comprises a collecting container in which the discharge electrode and the collecting electrode are arranged, and a pump for feeding the atmospheric air into the collecting container.

Further, in the above-mentioned method for measuring suspended particulate matter in the atmospheric air, it is preferable that the suspended particulate matter collected by the particulate collector is recovered onto the ground, and the predetermined measurement is conducted on the suspended particulate matter with the measuring apparatus.

Moreover, the above-mentioned method for measuring suspended particulate matter in the atmospheric air, preferably further comprising:

carrying the measurement apparatus onto the airplane, wherein the predetermined measurement is conducted on the collected particulate matter on the airplane.

In the present invention, the airplane includes not only an airplane and helicopter but also a balloon and airship which are called a light airplane.

In the present invention, suspended particulate matter in the atmospheric air is not collected by a filter so as to conduct various measurement on it but suspended particulate matter is electrically charged by single-pole ions emitted from a discharge electrode and the thus electrically charged suspended particulate matter is collected onto a surface of a collecting electrode having an electrical potential difference with respect to a discharge electrode. Therefore, compared with a case in which suspended particulate matter is collected by a filter, various measurements can be accurately conducted as follows. Further, when the above suspended particulate collecting device is conveyed to an arbitrary altitude being carried on an airplane, it becomes possible to measure suspended particulate matter at the arbitrary altitude.

For example, it is possible to use a collecting electrode, the surface of which is flat, so that suspended particulate matter can be attached onto the surface of the flat electrode. Therefore, compared with a case in which suspended particulate matter is collected by a filter, the individual particulates can be collected being dispersed. Accordingly, each single particulate can be easily irradiated with electromagnetic waves, which makes it easy to conduct various analyses on the suspended particulate matter. Further, in the case where a quantity of collected particulates are measured by measuring the weight before and after the collection of particulates, no errors are made by absorbing water, which is different from a case in which a filter is used for collecting particulates.

When the above particulate collecting device is carried onto an airplane and conveyed to an arbitrary altitude and driven to collect suspended particulate matter, it becomes possible to collect suspended particulate matter at the arbitrary altitude and conduct accurate measurement.

DETAILED DESCRIPTION OF THE INVENTION

Figure 1:
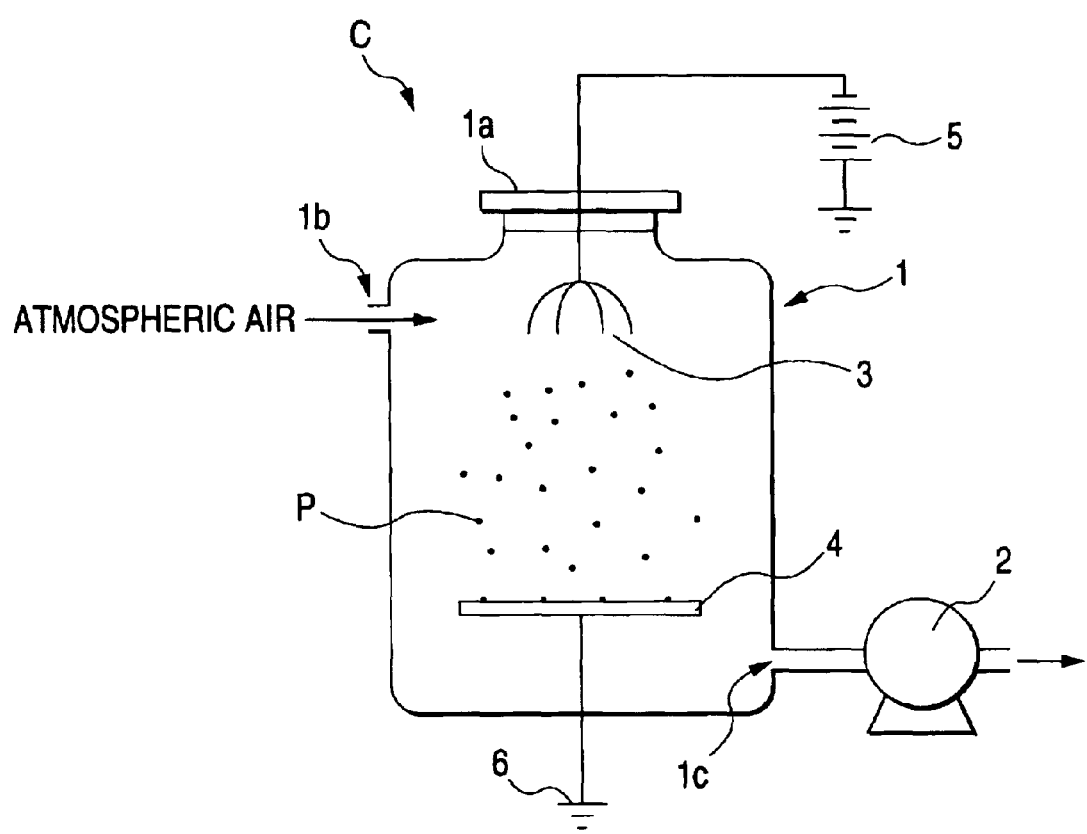
FIG. 1 is an arrangement view of particulate collector C used in an embodiment of the present invention.

Referring to the drawings, an embodiment of the present invention will be described below.

Figure 2:
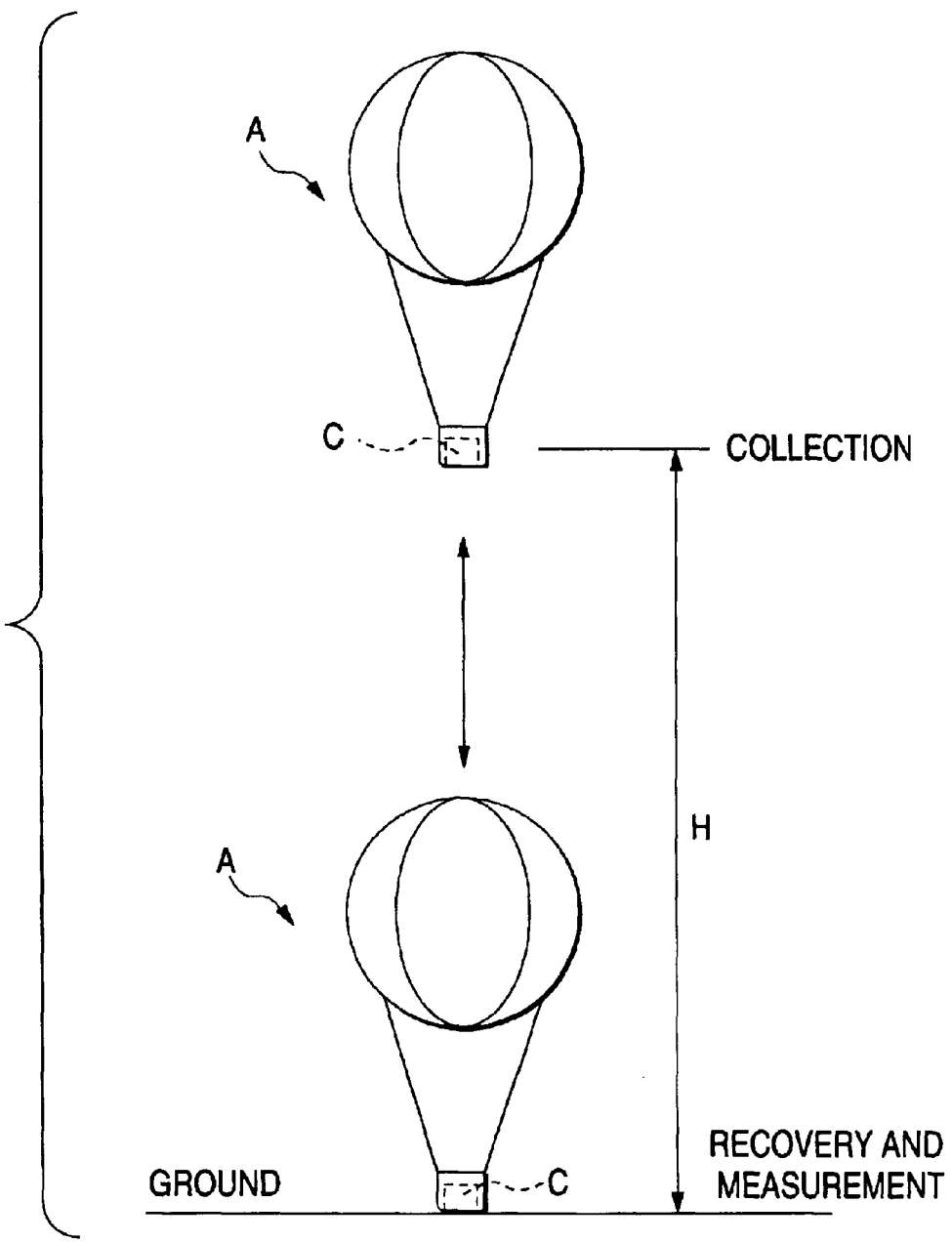
FIG. 2 is a schematic illustration of an example of a state in which particulate collector C shown in FIG. 1 is used.

FIG. 1 is an arrangement view showing a particulate collecting device used in an embodiment of the present invention, and FIG. 2 is a schematic illustration for explaining a state of use of the particulate collecting device.

Particulate collecting device C includes: a collecting container 1; a pump (compressor for collecting particulates) 2; a pair of electrodes 3, 4 arranged in the collecting container 1; and an electric circuit for giving an electrical potential to each electrode.

In the collecting container 1 provided with a cover 1a capable of being freely opened and closed, there are formed an inlet 1b from which the atmospheric air flows into the collecting container 1 and a communicating port 1c connected with a suction port of the pump 2. When the pump 2 is driven while the cover 1a is being closed, the atmospheric air is sucked into the collecting container 1 via the inlet 1b. In this collecting container 1, the discharge electrode 3 is arranged in its upper portion, and the collecting electrode 4 is arranged in its lower portion being opposed to the discharge electrode 3.

The discharge electrode 3 is impressed with a high voltage by a high voltage power source 5. Due to the foregoing, air in the periphery of the discharge electrode 3 is ionized, and single-pole ions are generated.

On the other hand, the collecting electrode 4 is a flat plate-shaped electrode, the surface of which is smooth. For example, the collecting electrode 4 is composed in such a manner that the surface of a metallic plate or a transparent plate such as a glass plate or resin plate is coated with a transparent electrode, and this collecting electrode 4 is connected with a grounding electric potential 6.

In the above constitution, when the discharge electrode 3 is impressed with a high voltage while the pump 2 is being driven, single-pole ions generated by ionization of air in the periphery of the discharge electrode 3 are moved to the collecting electrode 4 side by a difference in the electric potential between the discharge electrode 3 and the collecting electrode 4. While the single-pole ions are moving, they come into contact with suspended particulate matter P included in the atmospheric air within the collecting container 1. Therefore, particulate matter P can be electrically charged. By a difference in the electric potential between the discharge electrode 3 and the collecting electrode 4, the thus electrically charged suspended particulate matter P is moved to the collecting electrode 4 and collected onto the surface of the collecting electrode 4.

As exemplary shown in FIG. 2, the above particulate collector C is carried on airplane A such as a balloon. While the above particulate collector C is being conveyed at predetermined high altitude H, the pump 2 is being driven and the discharge electrode 3 is impressed with a high voltage. Due to the foregoing, suspended particulate matter P existing at high altitude H is collected by particulate collector C. After particulate collector C is driven for a predetermined period of time, airplane A such as a balloon is landed, and particulate collector C is recovered and the collecting electrode 4 is picked up. Then, suspended particulate matter P collected onto the surface of the collecting electrode 4 is subjected to the objective measurement.

In the case where suspended particulate matter P is observed through a microscope, when a surface of the collecting electrode 4, which is composed of a transparent plate such as a glass plate, is coated with a transparent electrode, suspended particulate matter P collected onto the surface of this collecting electrode 4 can be observed under the microscope as it is. Therefore, the profile and the number of suspended particulate matter P can be very simply measured.

In the case where a quantity of suspended particulate matter of a unit volume of the atmospheric air is measured, operation is conducted as follows. Before suspended particulate matter is collected, weight of the collecting electrode 4 in a clean state is measured with an electronic balance. In the case of collecting suspended particulate matter P, while a high voltage is being impressed upon the discharge electrode 3, the pump 2 is driven while a rate of flow is being maintained at a constant value. Due to the foregoing, a total volume of the atmospheric air fed into the collecting container 1 can be known from the rate of flow of the pump 2 and the period of time in which the pump is driven. At the point of time when the total volume of the atmospheric air fed into the collecting container 1 has reached a predetermined value, the pump 2 is stopped and airplane A is landed. Then, the collecting electrode 4 is picked up, and the weight is measured with an electronic balance. A difference in the weight before and after collecting suspended particulate matter represents the weight of suspended particulate matter existing in the atmospheric air fed into the collecting container 1.

In this measuring process, since the collecting electrode 4 is composed in such a manner that a metallic plate or a transparent plate such as a glass plate is coated with a transparent electrode, water is not absorbed by the collecting electrode 4 in the process of collecting suspended particulate matter P. Accordingly, no errors are made in the measurement, and a quantity of suspended particulate matter P can be accurately measured.

In the case where chemical substance contained in suspended particulate matter P in the atmospheric air is identified, since suspended particulate matter P, which has been collected, is located on a smooth plane being dispersed, the entire suspended particulate matter P can be easily extracted from the collecting electrode 4, and individual particulates can be also easily extracted.

Accordingly, by using one of or combination of a liquid chromatograph mass spectrometer, a gas chromatograph mass spectrometer, a high frequency induction combination plasma mass spectrometer, a spectrophotometer and a fluorescent X-ray analyzer, which are capable of identifying chemical substance, suspended particulate matter P collected in the above process is analyzed after it has been subjected to an appropriate pretreatment. Due to the foregoing, chemical substance contained in suspended particulate matter P can be precisely identified.

In the case of measuring a particle size distribution of suspended particulate matter P collected, a collecting electrode is used as the collecting electrode 4 which is composed of a transparent plate such as a glass plate, the surface of which is coated with a transparent electrode. When the above collecting electrode 4 is used, the transparent collecting electrode 4, onto which suspended particulate matter P has been collected, is irradiated with laser beams as it is by a laser diffraction particle size analyzer, so that a spatial intensity distribution of diffraction and scattering light can be measured and converted into the particle size distribution. In the case where the particle size distribution is measured with the above laser diffraction particle size analyzer, calibration is previously conducted on the surface of the collecting electrode 4 with reference particles contained in the unit area, the number of which has already been known. When calibration is previously conducted in this way, the concentration of suspended particulate matter P in the atmospheric air can be found from the absolute intensity of diffraction and scattering light obtained when laser beams are irradiated to the collecting electrode 4 which has collected suspended particulate matter P.

According to the above embodiment of the present invention, according to the flying altitude of airplane A such as a balloon on which particulate collector C is carried, it becomes possible to collect suspended particulate matter P existing at an arbitrary altitude. Therefore, an arbitrary measurement in the above measurement can be accurately made.

In the above embodiment, only particulate collector C is carried onto airplane A, and various measurement is made for the thus collected suspended particulate matter P after particulate collector C has been recovered onto the ground. However, it is possible to adopt a method in which an arbitrary measuring device in the above various measuring devices is carried on airplane A together with particulate collector C, and both the collection and the measurement of suspended particulate matter P are made in the air.

When the collection and the measurement of suspended particulate matter P are repeated at predetermined intervals, it becomes possible to continuously monitor a state of suspended particulate matter P in the atmospheric air at an arbitrary altitude.

When an altitude at which suspended particulate matter P in the atmospheric air is collected and measured is continuously changed, it becomes possible to measure and monitor a state of distribution of suspended particulate matter P in the atmospheric air in the vertical direction.

Concerning the collecting electrode 4 of particulate collector C, in the above embodiment, a collecting electrode is used which is composed of a metallic plate or a transparent plate such as a glass plate, the surface of which is coated with a transparent electrode, and suspended particulate matter P is attached to the surface of the solid electrode. However, depending upon an object of measurement, it is possible to adopt a method in which a dish-shaped collecting electrode made of conductive material in which liquid is accommodated is used and suspended particulate matter P, which has been electrically charged, is collected into the liquid. In this case, in the case where the particle size distribution is measured, it is possible to use a laser diffraction particle size analyzer which irradiates the leaser beam to the particulates in a state in which a group of particulates to be measured are dispersed in the liquid, that is, it is possible to use a laser diffraction particle size analyzer in the wet measurement. Alternatively, it is possible to use a dynamic scattering type particle size distribution measuring device.

In the present invention, of course, it is possible to use not only the aforementioned various measuring devices but also arbitrary measuring devices conforming to the object of measurement as a measuring device for measuring suspended particulate matter P collected by particulate collecting device C at an arbitrary altitude.

As described above, according to the present invention, when a particulate collector, in which suspended particulate matter in the atmospheric air is electrically charged by a discharge electrode and collected being attracted to a collecting electrode given an electric potential difference with respect to the discharge electrode, is carried onto an airplane such as a balloon, conveyed to an arbitrary altitude and driven, suspended particulate matter existing at an arbitrary altitude is collected and measured on the ground or airplane. Therefore, it is possible to measure suspended particulate matter existing at the arbitrary altitude. Further compared with a related-art method in which suspended particulate matter is collected with a filter, it becomes possible to make accurate measurement such as measurement of the profile, size and number of suspended particulate matter with a microscope. It also becomes possible to make measurement of a quantity of suspended particulate matter contained in the atmospheric air of the unit volume according to measurement of a difference in the weight of the collecting electrode before and after the collection of suspended particulate matter. It also becomes possible to make identification of chemical substance by various analyzers.

What is claimed is:

1. A method for measuring suspended particulate matter in the atmospheric air, the method comprising:

carrying a particulate collector onto an airplane, the particulate collector comprising a discharge electrode and a collecting electrode having an electric potential with respect to the discharge electrode;

conveying the particulate collector to an arbitrary altitude;

driving the particulate collector so as to collect the suspended particulate matter contained in the atmospheric air at the arbitrary altitude in such a manner that the suspended particulate matter is electrically charged by single-pole ions generated by the discharge electrode and the thus electrically charged particulates are attracted to the collecting electrode; and conducting a predetermined measurement on the collected particulate matter with a measuring apparatus according to an object.

2. The method for measuring suspended particulate matter in the atmospheric air according to claim 1, wherein the particulate collector comprises a collecting container in which the discharge electrode and the collecting electrode are arranged, and a pump for feeding the atmospheric air into the collecting container.

3. The method for measuring suspended particulate matter in the atmospheric air according to claim 1, wherein the suspended particulate matter collected by the particulate collector is recovered onto the ground, and the predetermined measurement is conducted on the suspended particulate matter with the measuring apparatus.

4. The method for measuring suspended particulate matter in the atmospheric air according to claim 2, wherein the suspended particulate matter collected by the particulate collector is recovered onto the ground, and the predetermined measurement is conducted on the suspended particulate matter on the ground.

5. The method for measuring suspended particulate matter in the atmospheric air according to claim 1, further comprising:

carrying the measurement apparatus onto the airplane, wherein the predetermined measurement is conducted on the collected particulate matter on the airplane.

6. The method for measuring suspended particulate matter in the atmospheric air according to claim 2, further comprising:

carrying the measurement apparatus onto the airplane, wherein the predetermined measurement is conducted on the collected particulate matter on the airplane.

7. An apparatus for measuring suspended particulate matter in the atmospheric air, the apparatus comprising:

a discharge electrode;

a collecting electrode having an electric potential with respect to the discharge electrode and including a metallic plate or a transparent plate coated with a transparent electrode;

a collecting container in which the discharge electrode and the collecting electrode are arranged;

a high voltage power source for impressing the discharge electrode with a high voltage so that air in the periphery of the discharge electrode is ionized; and a pump for feeding the atmospheric air into the collecting container.

8. The method for measuring suspended particulate matter in the atmospheric air according to claim 1 wherein the collecting electrode is a transparent plate coated with a transparent electrode and suspended particulate matter is collected onto the surface of said collecting electrode.

9. The method for measuring suspended particulate matter in the atmospheric air according to claim 1 further comprising the steps of:

before suspended particulate matter is collected, the weight of the collecting electrode is measured; and after suspended particulate matter is collected, the weight of the collecting electrode is measured.

10. The apparatus for measuring suspended particulate matter in the atmospheric air of claim 7, wherein particulate matter suspended within the atmospheric air pumped into the collecting container is collected and held on the collecting electrode.

* * * * *